United States Patent [19]

Olson

[11] 4,176,197
[45] Nov. 27, 1979

[54] METHOD FOR TREATING ACNE VULGARIS
[75] Inventor: B. Newell Olson, Norwich, N.Y.
[73] Assignee: Dominion Pharmacal, Inc., Norwich, N.Y.
[21] Appl. No.: 874,843
[22] Filed: Feb. 3, 1978
[51] Int. Cl.² .................... A61K 31/14; A61K 31/195
[52] U.S. Cl. ...................................... 424/319; 424/329
[58] Field of Search ................................ 424/319, 329

[56]  References Cited
U.S. PATENT DOCUMENTS

| | | | |
|---|---|---|---|
| 3,671,643 | 6/1972 | Kalopissis | 424/330 |
| 3,849,576 | 11/1974 | Kalopissis | 424/330 |
| 4,053,630 | 10/1977 | Yu et al. | 424/289 |

OTHER PUBLICATIONS

Handbook of Non-Prescription Drugs, pp. 155-160 (1973).

*Primary Examiner*—Leonard Schenkman

[57] ABSTRACT

The present invention relates to treatment of dermatological conditions. In more particular, it relates to the use of oxygen potentiating compositions not heretofore employed or recognized as effective in the treatment of acne vulgaris and related dermatological conditions. The compositions comprise, as active ingredients, a combination of a cationic surface active quaternary ammonium halide and a thio-amino compound.

3 Claims, No Drawings

METHOD FOR TREATING ACNE VULGARIS

BACKGROUND OF THE INVENTION

Acne vulgaris has been a problem for many people for many centuries. It has its most common occurrence during puberty. For this reason, many theories have been advanced as to its root cause. These theories range from faulty metabolism of lipids to hyperactivity of the pilosebaceous system. See Sutton, R. L., Jr., Acne Vulgaris, South, M. J., 34; 1071 (1941): and Faust, R. R., et al., Acne Vulgaris, Medical Times, June (1961). Many other theories have also been advanced as to the cause of acne. However, to date none seems totally supported by the medical community. As a consequence, many different type products are tried, and often rejected, by acne sufferers in their attempt to control this condition before facial disfigurement occurs. The present invention has now found, quite unexpectedly, a new type liquid composition having unusual effectiveness in the treatment of acne vulgaris, and in accordance therewith, appears to have uncovered the root cause of this condition as well.

It is, therefore, an object of this invention to provide a liquid composition that exhibits a high order of effectiveness in the treatment of acne vulgaris and related dermatological condition.

SUMMARY OF THE INVENTION

The present invention combines a cationic quaternary ammonium halide with an oxygen potentiating compound in liquid solution. In the development of this solution, it appears the root cause of acne vulgaris has been unexpectedly uncovered. The term used to describe this cause is "anaerobiosis" which is defined by this invention to mean "life without oxygen". In this invention, it was found that anaerobic-type bacteria are primarily responsible for acne type blemishes. These organisms were found to exist deep within pores and other recesses of the skin where they are protected from exposure to oxygen and where they appear to receive nourishment from facial body fluids. During puberty these fluids are composed of a rich blend of particular hormones, partial sugars and fatty acids. Thus, it appears that the teenager is most afflicted due to the particular nutritional blend of these fluids which benefit anaerobic growth of these type bacteria. Many products now used by the acne sufferer comprise creams, lotions and other film-forming products which can form occlusive dressings over the skin thus excluding normal oxygen exposure to the skin.

The present invention has found that oxygen potentiation to the skin is required in successful acne treatment and that effective anti-microbic agents must encompass broad spectrum potential for combating anaerobic-type microbes. It is recognized that many of these type microbes are difficult to kill even on skin surfaces and when protected by the natural fat of pores and glandular orifices, the task is extremely difficult. To overcome this problem, strong germicides have been used in the past. Some of these type products can coagulate blood serum and thereby provide even further protection to microbes in the wound.

PREFERRED EMBODIMENT OF THE INVENTION

In the preferred embodiment of the invention, two essential active components are combined in aqueous solution. The major active component is a cationic surface active quaternary ammonium halide. Typical examples of these comprise diisobutylphenoxyethoxyethyldimethylbenzyl ammonium chloride, alkyldimethylbenzyl ammonium chloride, diisobutylcresoxyethoxyethyldimethylbenzyl ammonium chloride, alkyl trimethyl ammonium chloride, carboxypentadecyltrimethyl ammonium chloride, phenoxyethyldimethyldodecyl ammonium bromide, bis-quaternary ammonium chloride, bis-quaternary ammonium bromide, and other derivatives thereof. The preferred members of this group comprise quaternary ammonium compounds of the group octyl aryloxyethoxyethyldimethylbenzyl ammonium chloride wherein the aryloxy group is phenoxy or cresoxy.

The second active component is selected from the groups comprising the thio-amino acids, N-acetyl derivatives of thio-amino acids, and chemical complexes of thio-amino acids and allantoin. Preferred members comprise cystine, cysteine, methionine, N-acetyl cystine, N-acetyl cysteine, N-acetyl DL Methionine, allantoin N-acetyl cystine, allantoin N-acetyl cysteine, allantoin N-acetyl DL methionine, aluminum hydroxy allantoin N-acetyl cystine, aluminum hydroxy allantoin N-acetyl cysteine, aluminum hydroxy allantoin N-acetyl DL Methionine, aluminum chlorhydroxy allantoin N-acetyl cystine, aluminum chlorhydroxy allantoin N-acetyl cysteine, aluminum chlorhydroxy allantoin N-acetyl DL methionine, and the like.

In a method of use of the composition of this invention, the acne affected area of the skin is first thoroughly cleansed with soap, alcohol or other cleansing materials. The composition is then applied with a suitable application means and allowed to air dry on the skin. A re-application of the composition after a drying period of several minutes will provide improved results. Alternatively, the liquid composition can be used for cleansing affected parts prior to application of a final thin surface covering which is allowed to remain on the skin to air dry.

The preferred compositions can advantageously contain ingredients in addition to the two active ingredients. These ingredients may be incorporate in order to enhance stability, color, odor and cleansing ability or to adjust to a proper pH. Stability can be enhanced by incorporating a small amount of a non-ionic surface active agent such as condensates of sorbitan monostearate with about 20 moles of ethylene oxide such as the "Tween" compounds available from ICI American, Inc., condensates of ethylene oxide with propylene oxide condensates of propylene glycol available under the trade-name "Pluronics" from BASF Wy andotte Corporation, fatty alcohol ethoxylates such as the "Siponic" compounds available from Alcolac, Inc., and the like. Color can be enhanced using any one of a number of water-soluble FD&C-type colorants. These materials are commercially available. Cleansing ability of the preferred compositions is increased by incorporating a lower chain alcohol such as those having a carbon chain from 1 to 5 carbon atoms. Preferred members comprise ethanol and isopropanol.

The instant compostions normally have a pH between 3 and 7. Preferably, the final pH is on the order of from 3.5 to 5.5. Suitably, a buffering system may be employed to assure maintenance of a pH within the aforesaid range to assure continued potency of the composition. In other instances, adjustment of pH using sodium hydroxide, potassium hydroxide or other alkaline materials can result in a stable system. Acidifying agents can be used to adjust to proper pH. These include acetic acid, citric acid, potassium dihydrogen phosphate, and hydrochloric acid. Chelating agents can be employed for pH adjustment purposes. These can include ethylenediamine tetraacetic acid or the alkali metal salt thereof such as disodium or tetrasodium.

The present use composition has been found to be effective in combating acne vulgaris and other dermatological conditions involving certain anaerobic and facultative anaerobic-type bacteria. Bacteria to which I refer belong to groups of anaerobic microbes comprising Clostridia, gram-positive anaerobic cocci, gram-negative anaerobic cocci, gram-positive nonsporeforming anaerobic bacilli, and gram-negative nonsporeforming anaerobic bacilli. These type bacteria are described by Blair, J. E., et al., Manual of Clinical Microbiology, published by The American Society of Microbiology, Bethesda, Maryland (1970). Many of these microbes are known to be normal flora of the skin. Many are known to be capable of invading broken skin and, in accordance with this invention, have been found to be capable of colonizing within pores, hair follicles and glandular skin openings.

The following specific examples are further illustrative of the nature of the present invention, but it is to be understood that the invention is not limited thereto. The compositions of these examples are prepared in the usual way. All amounts and proportions in these examples are by weight unless otherwise specified.

EXAMPLE I

| Liquid Treating Solution | | |
| --- | --- | --- |
| | Ingredients | Amounts |
| 1. | De-ionized water | 96.93 |
| 2. | Sorbitan Monostearate condensate | 2.500 |
| 3. | Diisobutylcresoxyethoxyethyl-dimethylbenzyl ammonium chloride | 0.100 |
| 4. | N-acetyl cysteine | 0.250 |
| 5. | Ethylenediamine tetraacetic acid - tetrasodium salt - q.s. | 0.100 (approx.) |
| 6. | FD&C Yellow #6 (1% solution) | 0.120 |

The ingredients are added in order of appearance with slow stirring. Ingredient 5 was added in sufficient quantity to adjust to a final pH of 4.6.

The liquid solution was applied to acne affected skin in accordance with the invention.

EXAMPLE II

| Liquid Treating Solution | | |
| --- | --- | --- |
| | Ingredients | Amounts |
| 1. | De-ionized water | 70.180 |
| 2. | Pluronic L-64 | 3.100 |
| 3. | Isopropyl alcohol | 26.000 |
| 4. | diisobutylphenoxyethoxyethyl-dimethylbenzyl ammonium chloride | 0.130 |
| 5. | Allantoin N-acetyl DL methionine | 0.250 |
| 6. | Sodium Hydroxide (1 N) | 0.340 (approx.) |

Ingredients were mixed in order of appearance with continued slow stirring. Sufficient sodium hydroxide was added to adjust to a final pH of 4.2.

The solution was applied to acne affected areas in accordance with the invention.

To demonstrate the efficacy of the liquid solutions of this invention in the treatment of acne vulgaris, the following representative clinical case histories are submitted.

Case Number 1

A White male teenager, age 16, suffering from acne vulgaris received application of the liquid solution of Example I twice daily and prior to bed time. Careful cleansing of the face with mild soap and warm water was carried out before each application. A definite improvement in the condition was noted within 5 days as evidenced by reduced redness around pustules and lesions with several typical acne comedones becoming dried and healed.

Case Number 2

A white female, age 15, suffering from acne vulgaris was given daily applications of the solution of Example II for a period of seven days. Applications were made to a soap and water cleansed face once each morning and once each night prior to bed time. After the seven day period, the acne vulgaris was noted to be under control with definite improvement in overall appearance of facial skin. Followng the seven day period, the patient noted slight drying of the skin. She, therefore, began applying a film-forming moisturizing lotion to the acne affected areas. A relapse of acne vulgaris occurred which cleared up after termininating use of the lotion. Continued use of the solution of Example II maintained control of the acne condition with progressive improvement with time.

Case Number 3

A white female, age 31, suffering from mild bouts of acne vulgaris a few days prior to each menstrual period, applied the hydro-alcoholic treating solution of Example II to facial area normally affected. Applications were made three times daily beginning 5 days prior to normal onset of acne condition. Applications of the solution continued through the menstrual cycle. No noticeable acne vulgaris developed during the application period.

Case Numbers 4–16

Twelve teenage boys and girls, randomized regarding degree of acne involvement, were each provided with 4 oz. plastic bottles of treating solution of Example II. Instructions provided were in accordance with methodology of this invention. Dermatological condition improved in all patients.

It is apparent from the foregoing case histories that the liquid solutions of this invention comprise a valuable tool in the treatment of acne vulgaris and related dermatological conditions. The exact mechanism of action of the inventive solutions is not known. What is known is that the solutions of this invention exert a beneficial effect in the treatment of acne vulgaris and related dermatological conditions by possessing an unexpected potential for penetrating into pores, glandular orifices and various skin recesses. Since anaerobic microbes have been found to be primarily responsible for acne blemishes, it seems apparent that the solutions, unexpectedly, combine ability to penetrate areas where blemishes occur while at the same time exerting a cidal effect due to incease of oxygen potential within the blemish area. The beneficial effect noted in applications of instant use solutions is greater than what would be expected from application of either the cationic surface-active quaternary agent or the thio-amino compound alone. Accordingly, this invention has as its unexpectedness, the synergistic effect obtained by the instant liquid solutions in the treatment of acne vulgaris and related dermatological conditions. The term "oxygen potentiation" as used herein, is meant to describe the apparent unexpected cidal effect of the use solutions on aerobic as well as anaerobic-type microbes.

In-vitro studies of the liquid treating solutions of this invention have shown unusual potency as measured by zones of inhibition around product impregnated paper discs according to well establised microbiological techniques. Using well known commercially available anti-acne products purchased through trade channels, a direct comparison of zone size against the composition of Example II herein was carried out. Results of these studies are shown in the following examples.

EXAMPLE III

A pour plate of Mueller-Hinton agar purchased from BBL Corporation of Cockneyville, Maryland, was prepared using an American Type Culture Collection (ATCC) of Staphlococcus aureus. Four filter paper discs purchased from BBL, each having a diameter of 10 millimeters, were placed flat on the surface of the agar equal distance apart. 0.05 Milliliter of each of the following products was placed on the surface of each disc. The plates were then stored in inverted position at 37 degrees centigrade for 48 hours. The clear zone of inhibition surrounding each disc was then measured with the following results.

| Product | Zone of Inhibition |
|---|---|
| Commercial anti-acne product containing isopropanol and allantoin - | 0 |
| Commercial anti-acne product containing isopropanol and benzoic acid - | 0 |
| Liquid Treating Solution of Example II - Fresh made - | 20 mm |
| Liquid Treating Solution of Example II - Aged two weeks at 39 degrees centigrade - | 20 mm |

These data show the liquid treating solution of this invention to be highly potent against aerobic Staphlococcus aureus microbes. In comparison to two commercially available anti-acne products, the liquid treating solution of this invention showed obvious superiority. Incorporation of fresh and aged solutions showed that the instant solutions do not loose potency after prolonged exposure to elevated temperatures.

EXAMPLE IV

To ascertain the effectiveness of the liquid treating solutions of Example II against anaerobic-type Propionibacterium acnes, strain ATCC, the following in-vitro tests were run.

Propionibacterium acnes was inoculated on separate plates containing BBL purchased Mueller-Hinton agar and BBL purchased nutrient agar with 10% sheep's blood. Inoculation comprised spreading 0.05 milliliter of an overnight nutrient broth culture of the organism with a cotton swab. BBL pruchased paper discs were placed flat on the agars. 0.05 Milliliter of the solutions to be tested were placed on respective discs. The plates were incubated in a BBL Gas-Pak anaerobic jar at 37 degrees centigrade for 48 hours and 96 hours for the sheep blood agar and the Mueller-Hinton agar, respectively. The diameter of the zone size surrounding each disc was then read in millimeters.

| Product | Sheep's Blood Agar | Mueller-Hinton Agar |
|---|---|---|
| Commercial product containing isopropanol and allantoin - | No zone | No zone |
| Commercial product containing isopropanol and benzoic acid - | No zone | No zone |
| Liquid Treating Solution of Example II - | 26 mm | 45 mm |

EXAMPLE V

In another trial to ascertain effectiveness of the liquid treating solution of this invention against established acne causing microbes the following in-vitro test was conducted.

Brain/heart infusion broth with 0.1% agar was prepared and placed in deep tubes. Each tube was then inoculated with 0.001 milliliter of an overnight nutrient broth culture of Propionibacterium acnes (ATCC). The following solutions to be tested were then added to respective tubes followed by incubation at 37 degrees centigrade for 96 hours. Bacterial growth, or lack of it, was an indication of effectiveness of each test solution against the P. acnes organism.

| Test Solution | Degree of Growth |
|---|---|
| Control (No test solution) | +++ Extensive growth |
| Commercial product containing isopropanol and allantoin- | +++ Substantial growth |
| Commercial product containing isopropanol and benzoic acid- | + Slight growth |
| Liquid Treating Solution of Example II- | No growth |

These data show clearly the effectiveness of the liquid treating solution of this invention against the anaerobic-type microbe, Propionibacterium acnes. One leading commercial product showed substantially less effectiveness than the solution of this invention while the other commercial product showed only slight improvement over the control which had no test solution added.

In the practice of this invention, it has been found that effectiveness can be enhanced by incorporating into the solution small amounts of aluminum chlorhydroxide and salts of aluminum chlorhydroxide such as aluminum chlorhydroxide allantoinate. Compounds of this type are commercially available from Schuylkill Chemical Company of Philadelphia, Pennsylvania.

For purposes of illustration, specific examples and description of the invention are offered herein. Numerous variations can be made with respect to the particular materials and amounts employed without departing from the spirit of the invention. It is desired, therefore, to be limited only to the scope of the appended claims.

I claim:

1. A method of treating patients afflicted with acne which comprises topically applying to the skin of said patients a liquid solution consisting essentially of allantoin N-acetyl DL methionine complex in the order of 0.25 percent and quaternary ammonium chloride in the order of 0.13 percent and sufficient alkali to produce a final pH in the range of from pH 3 to 7.

2. The method of claim 1 wherein said quaternary ammonium chloride is diisobutylphenoxyethoxyethyldimethylbenzyl ammonium chloride.

3. The method of claim 1 wherein said alkali is a solution of tetra sodium salt of ethylenediamine tetra acetic acid.

* * * * *